United States Patent
Kubo et al.

(10) Patent No.: US 9,125,602 B2
(45) Date of Patent: Sep. 8, 2015

(54) MEASUREMENT DEVICE

(75) Inventors: Masayuki Kubo, Kyoto (JP); Kiyoaki Ishiguro, Kyoto (JP)

(73) Assignee: ARKRAY, INC., Kyoto (JP)

( * ) Notice: Subject to any disclaimer, the term of this patent is extended or adjusted under 35 U.S.C. 154(b) by 870 days.

(21) Appl. No.: 12/450,680

(22) PCT Filed: Apr. 25, 2008

(86) PCT No.: PCT/JP2008/058131
§ 371 (c)(1),
(2), (4) Date: Oct. 6, 2009

(87) PCT Pub. No.: WO2008/136437
PCT Pub. Date: Nov. 13, 2008

(65) Prior Publication Data
US 2010/0137697 A1 Jun. 3, 2010

(30) Foreign Application Priority Data

Apr. 27, 2007 (JP) .................................. 2007-118135

(51) Int. Cl.
A61B 5/00 (2006.01)
A61B 5/145 (2006.01)

(52) U.S. Cl.
CPC ........... *A61B 5/14532* (2013.01); *A61B 5/7445* (2013.01)

(58) Field of Classification Search
CPC ............. A61B 5/7445; A61B 5/14532; A61B 2562/0295; G06F 19/345; G06F 19/24; G01N 27/3272; G01N 33/66; C12Q 1/006
USPC ............................. 600/345, 347, 365; 702/19
See application file for complete search history.

(56) References Cited

U.S. PATENT DOCUMENTS

| 2004/0094433 A1* | 5/2004 | Neel et al. ................. 205/777.5 |
| 2007/0276209 A1* | 11/2007 | Emoto et al. ................. 600/319 |
| 2008/0194934 A1* | 8/2008 | Ray et al. ....................... 600/347 |

FOREIGN PATENT DOCUMENTS

| JP | 07-128338 A | 5/1995 |
| JP | 11-56822 A | 3/1999 |
| JP | 2001-221803 A | 8/2001 |
| JP | 2004-184255 A | 7/2004 |
| JP | 2005-198790 A | 7/2005 |
| JP | 2006-109895 A | 4/2006 |
| JP | 2007-37822 | 2/2007 |
| WO | WO-01/93143 A | 12/2001 |
| WO | WO-2005/106446 A | 11/2005 |

OTHER PUBLICATIONS

International Search Report mailed on Jun. 3, 2008.

* cited by examiner

*Primary Examiner* — Michael D'Angelo
*Assistant Examiner* — Christian Jang
(74) *Attorney, Agent, or Firm* — Fishman Stewart Yamaguchi PLLC

(57) ABSTRACT

A measurement device A includes a display section 10 capable of displaying measurement data obtained by measurement means 12, 13, 14a, a clock function section 16, an event time setting means 14b, 15 capable of setting the time of an event, and an elapsed time display processing means 14c that starts measurement of the elapsed time from the time of the event to the current time when the time of the event is set by the event time setting means and causes the display section 10 to display the elapsed time. With this arrangement, the user does not need to perform a troublesome task of calculating the elapsed time, and the measurement of a sample in a proper period of time after the event is promoted.

14 Claims, 4 Drawing Sheets

MEASUREMENT DEVICE

TECHNICAL FIELD

The present invention relates to a measurement device for use in measuring bio data such as a blood glucose level.

BACKGROUND ART

An example of conventional measurement device is disclosed in Patent Document 1. The measurement device includes a measurement means capable of measuring a blood glucose level, a means for determining the date and time of the measurement of the blood glucose level, and a display means for displaying the measurement data on the blood glucose level and the data on the measurement date and time. The measurement device further includes an operation means capable of selectively inputting information as to whether the measurement of the blood glucose level is performed before or after a meal. With this arrangement, when the user or a doctor checks the measurement data, the user or the doctor can find whether the measurement data is obtained from measurement performed before or after a meal, which is suitable for proper evaluation of the measurement data.

However, there is still room for improvement in the conventional technique.

Specifically, the user is sometimes instructed by e.g. a doctor to measure the blood glucose level in a predetermined period of time from a meal. However, the above-described measurement device has no function to display the time elapsed from the meal on a screen. Thus, in order for the user to follow the doctor's instruction, the user needs to remember the time at which the user had the meal and calculate how much time has elapsed from the meal based on the time of the meal and the current time. These tasks are troublesome. Further, the user may forget or mistake the time of the meal. In such a case, there is a high possibility that the measurement of the blood glucose level is performed in an improper period of time.

Patent Document 1: JP-A-2007-37822

DISCLOSURE OF THE INVENTION

Problems to be Solved by the Invention

An object of the present invention is to provide a measurement device which is capable of solving or lessening the above-described problems.

Means for Solving the Problems

To solve the above-described problems, the present invention takes the following technical measures.

A measurement device provided according to the present invention includes a measurement means that performs measurement on a particular component contained in a sample, a display section capable of displaying measurement data obtained by the measurement means, a clock function section, an event time setting means capable of setting a time of an event related to the measurement, and an elapsed time display processing means that starts measurement of the elapsed time from the time of the event to the current time when the time of the event is set by the event time setting means and causes the display section to display the elapsed time.

Preferably, the elapsed time is displayed on a standby screen of the display section. The "standby screen", as used herein, is a screen displayed on the display section when the measurement device of the present invention is in a standby state in which the measurement device is not performing measurement or in a state in which the measurement device is not performing a particular function.

Preferably, the measurement device according to the present invention further comprises a notification means capable of performing a notifying operation in a manner that is different from the displaying of the data by the display section. The notification means performs the notifying operation when a first predetermined period of time has elapsed from the time of the event.

Preferably, the displaying of the elapsed time is stopped when a second predetermined period of time has elapsed from the time of the event.

The second predetermined period of time can be set independently of the first predetermined period of time and may be equal or unequal to the first predetermined period of time.

Preferably, the elapsed time display processing means calculates the elapsed time based on the time of the event and the current time clocked by the clock function section. The displaying of the elapsed time is stopped when the time clocked by the clock function section is changed within a period during which the elapsed time is displayed.

Preferably, the measurement device according to the present invention further comprises a storage means in which the measurement data obtained by the measurement means is to be stored. When the measurement data is obtained from the measurement performed before the elapse of a third predetermined period of time from the time of the event, reference data indicating to that effect is stored in the storage means as attached to the measurement data.

The third predetermined period of time can be set independently of the first predetermined period of time and the second predetermined period of time and may be equal or unequal to the first predetermined period of time and the second predetermined period of time.

Preferably, the measurement device according to the present invention further comprises a terminal section capable of reading the measurement data obtained by the measurement means and the reference data out of the storage means and outputting the measurement data and the reference data to an external device.

Preferably, when a predetermined operation is performed, the event time setting means regards the time when the operation is performed as the time of the event.

Preferably, the measurement device according to the present invention further comprises an operation switch, and the predetermined operation is an operation to turn on the operation switch.

Preferably, the measurement means includes a sensor mount portion to which a sensor capable of retaining the sample is to be mounted, and a detection switch for detecting the mounting of the sensor to the sensor mount portion. The predetermined operation is an operation to mount the sensor to the sensor mount portion to cause the detection switch to detect the mounting of the sensor.

Preferably, when the predetermined operation is performed a plurality of times, the time when the operation is performed last is regarded as the time of the event, and data having been regarded as the time of the event earlier than that time is invalidated.

Preferably, the measurement device according to the present invention is provided with an edit function capable of changing at least one of the value representing the time of the event and the value representing the elapsed time by a predetermined operation.

Preferably, the measurement device according to the present invention includes a case having a size allowing the case to be held with one hand, and the display section is attached to the case so as to be viewable from outside. The case accommodates therein devices forming the measurement means, the clock function section, the event time setting means and the elapsed time display processing means, and the entirety of the measurement device is designed as a portable measurement device.

Preferably, the measurement means, the event time setting means and the elapsed time display processing means comprise a CPU and a storage means attached to the CPU.

Preferably, the measurement means is capable of measuring a blood glucose level, and the event is a meal.

Other features and advantages of the present invention will become more apparent from the detailed description given below with reference to the accompanying drawings.

BEST MODE FOR CARRYING OUT THE INVENTION

Preferred embodiments of the present invention will be described below with reference to the accompanying drawings.

Figure 1:
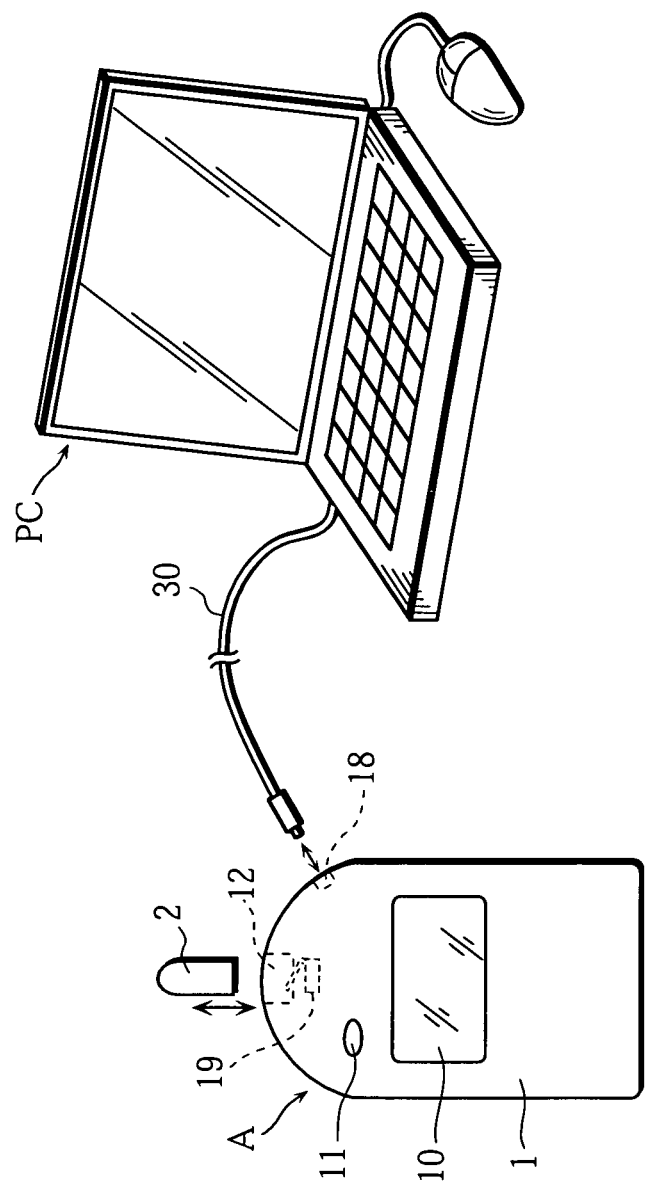
FIG. 1 illustrates an appearance of an example of measurement device according to the present invention.
Figure 2:
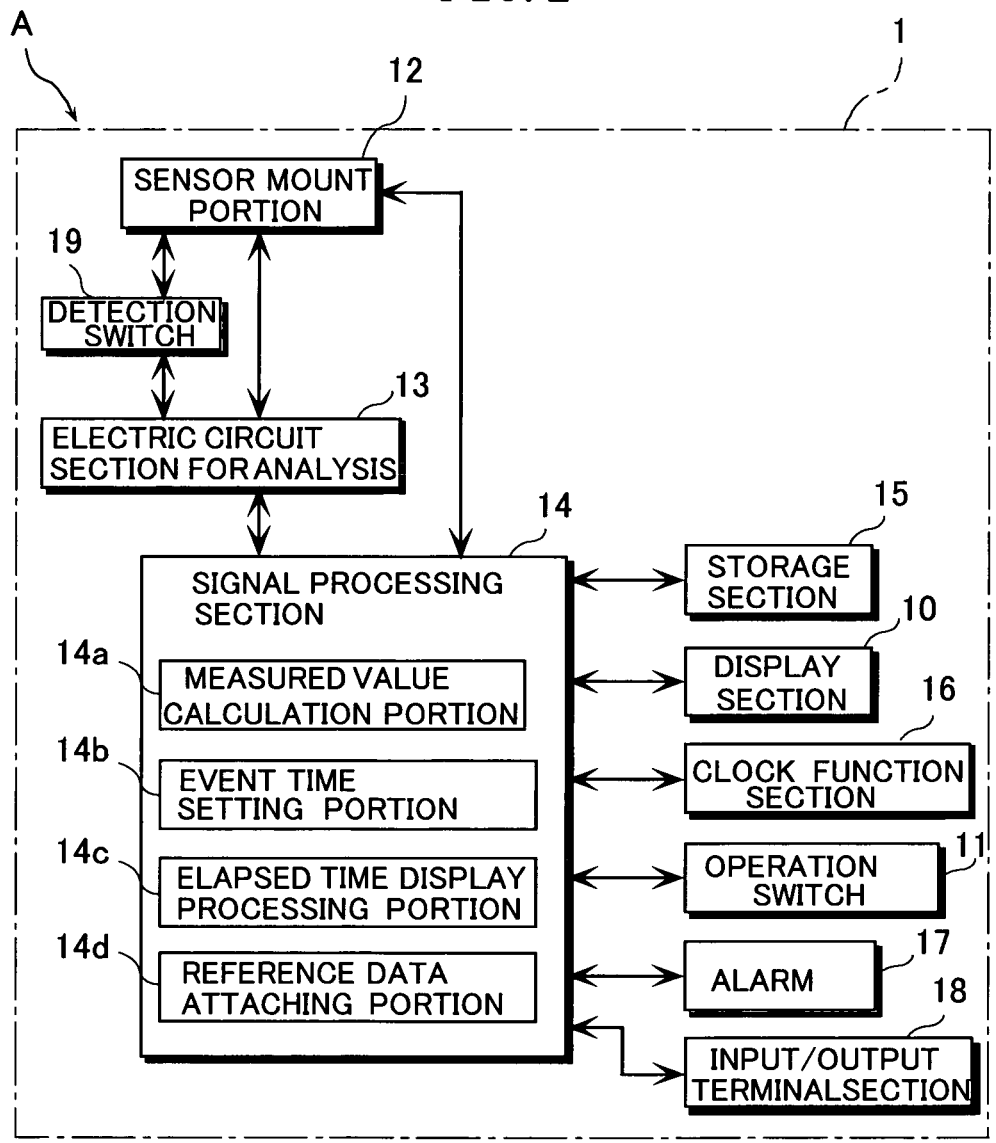
FIG. 2 is a block diagram of the measurement device shown in FIG. 1.

FIGS. 1 and 2 show an example of measurement device according to the present invention. The measurement device A of this embodiment is designed to measure a blood glucose level. As better shown in FIG. 1, the measurement device A includes a case 1 which has a size and shape suitable for holding and carrying with one hand. On an outer surface of the case 1, a display section 10 capable of displaying images and an operation switch 11 are provided. The display section 10 is formed using a liquid crystal display, for example. The measurement device A is capable of measuring the glucose level of blood by using a sensor 2 in the form of a strip for blood sampling.

As better shown in FIG. 2, in addition to the display section 10 and the operation switch 11, the measurement device A includes a sensor mount portion 12, a detection switch 19, an electric circuit section for analysis 13, a signal processing section 14, a storage section 15, a clock function section 16, an alarm 17, and an input/output terminal section 18. The signal processing section 14 comprises a CPU, for example. From the functional viewpoint, the signal processing section 14 comprises a measured value calculation portion 14a, an event time setting portion 14b, an elapsed time display processing portion 14c and a reference data attaching portion 14d.

The sensor mount portion 12 is a portion to which the sensor 2 is to be removably mounted. The case 1 includes an end formed with a hole for receiving the sensor 2, and the inside of the hole is the sensor mount portion 12. The detection switch 19 serves to determine whether or not the sensor 2 is mounted to the sensor mount portion 12. When the sensor 2 is mounted to the sensor mount portion 12, the detection switch is turned on by being pressed by the sensor 2.

When blood is applied to a predetermined portion of the sensor 2 mounted to the sensor mount portion 12, the electric circuit section for analysis 13 applies a voltage to the sensor to generate a response current corresponding to the concentration of glucose in the blood. The electric circuit section for analysis 13 converts the response current to a voltage and inputs the voltage signal to the signal processing section 14. The measured value calculation portion 14a of the signal processing section 14 calculates the glucose level based on the voltage signal. Such a technique of measuring the glucose level is known (see e.g. Japanese Examined Patent Application Publication No. 8-10208). The glucose level can be measured by a technique which is different from this embodiment. The combination of the sensor mount portion 12, the electric circuit section for analysis 13 and the signal processing section 14 (the measured value calculation portion 14a) is an example of measurement means defined by the present invention.

The storage section 15 includes RAM and EEPROM for storing glucose level measurement data and other various data to be described later, as well as ROM storing control programs for the signal processing section 14. Preferably, the clock function section 16 has a calendar function to find the current date and is so designed that the time is adjustable. The input/output terminal section 18 is provided for connection to e.g. a personal computer PC via a cable 30, as shown in FIG. 1. When the measurement device A is connected to the personal computer PC, it is possible to change the setting of each part of the measurement device A and transfer the data stored in the storage section 15 to the personal computer PC by accessing the signal processing section 14 from the personal computer PC.

When the operation switch 11 is pressed, the event time setting portion 14b regards the time of press as the time of an event and stores the data on that time in the storage section 15. However, the measurement device A is designed to be switchable between an event input setting ON mode in which the setting of the event time by the operation switch 11 is rendered valid and an event input setting OFF mode in which such setting is rendered invalid. Such switching can be achieved by rewriting data by using the personal computer PC, for example. The combination of the signal processing section 14 (the event time setting portion 14b) and the storage section 15 is an example of event time setting means defined by the present invention. The elapsed time display processing portion 14c calculates the time elapsed from the time of the event to the current time and causes the display section 10 to display the calculation result. In storing the measured value of the glucose level in the storage section 15, the reference data attaching portion 14d attaches predetermined reference data to the measurement data under certain conditions. The above-described operation of the signal processing section 14 will be specifically described later.

The operation and advantages of the measurement device A are described below. An example of process carried out by the signal processing section 14 is also described referring to the flow chart shown in FIG. 4.

Figure 3A:
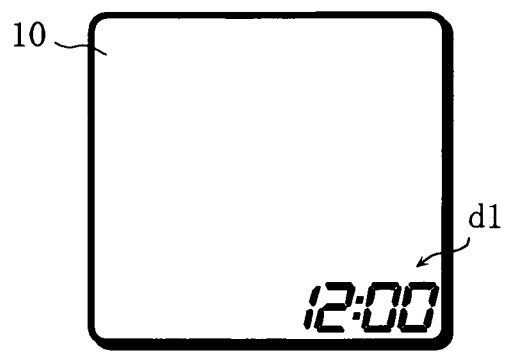
FIGS. 3A to 3C each is a front elevational view illustrating an example of screen displaying in the measurement device shown in FIG. 1.

When the measurement device A is not used, the display section 10 is set in an off state for saving power. However, as indicated by the reference sign d1 in FIG. 3A, the current time can be displayed on the standby screen of the display section by selecting a clock display function. When the user presses the operation switch 11 in the event input setting ON mode, the signal processing section 14 regards the time of press as the time of the event and stores the time of the event in the storage section 15 (S1: YES, S2: YES, S3). The event may be a meal, for example. In this case, the user operates the operation switch 11 just after eating a meal. Alternatively, the operation switch 11 may be operated before or during a meal.

Then, the signal processing section 14 starts to calculate the time elapsed from the time of the event to the current time and causes the display section 10 to display the elapsed time and a predetermined reference mark on the standby screen of the display section 10 (S4, S5). The definition of the standby screen has been described before. The elapsed time is displayed in such a manner as indicated by the reference sign d2 in FIG. 3B and updated every one minute, for example. The reference mark may be a pattern of a fork, as indicated by the reference sign d3. The reference mark is displayed to indicate that the current time is still within a predetermined period of time from the time of the event.

According to the process described above, since the time elapsed from a meal is displayed on the display section 10, the user can easily find the elapsed time by looking at the display. Thus, the user becomes free from troublesome tasks of remembering the time of a meal and calculating, after eating the meal, the elapsed time based on the time of the meal and the current time. Thus, the measurement at an improper time due to the user's forgetting or mistaking the time of the event is prevented. Moreover, by checking the reference mark indicated by the reference sign d3, the user can easily find that the current time is still within the predetermined period of time from the meal.

When a first predetermined period of time (e.g. two hours) has elapsed from the time of the event, the signal processing section 14 causes the alarm 17 to sound an alarm (S6: YES, S7). The value of the first predetermined period of time, which is stored in the storage section 15 in advance, may be a period of time from the time of the meal to the time to measure the blood glucose level. Thus, by hearing the alarm, the user is properly notified that the time to measure the blood glucose level has come. Thus, the user is prevented from forgetting to measure the blood glucose level in a predetermined period of time. Preferably, the value of the first predetermined period of time can be changed by operating the operation switch 11 or by performing a writing operation by way of the personal computer PC. This holds true for a second predetermined period of time in step S8, which is described below.

Figure 3B:
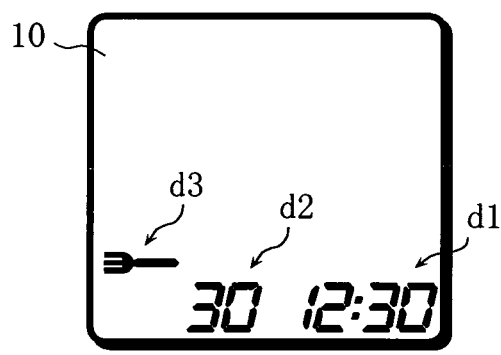

When the second predetermined period of time (e.g. three hours) has elapsed from the time of the event, the signal processing section 14 stops displaying the elapsed time and the reference mark indicated by the reference signs d2 and d3 in FIG. 3B (S8: YES, S9). Since the blood glucose level returns to a usual value (in a fasting state) after elapse of e.g. about three hours, displaying the elapsed time is practically meaningless. The above-described process properly accommodates such cases. Even when the second predetermined period of time has not elapsed yet, the signal processing section stops displaying the elapsed time and the reference mark in a manner similar to the above when the time set in the clock function section 16 is changed (S8: NO, S14: YES, S9). In spite of the time change, if the elapsed time is calculated based on the time indicated after the time change and the time of the meal inputted before the time change, the value obtained by the calculation is likely to be incorrect. By the above-described process, however, such an elapsed time, which is likely to be incorrect, is prevented from being displayed on the display section 10.

Figure 3C:
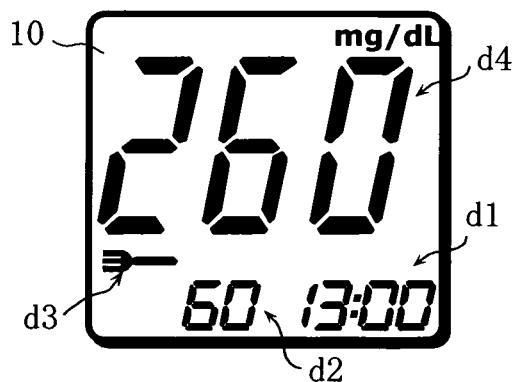

When the blood glucose level is measured before the elapse of the second predetermined period of time from the time of the event without changing the time setting in the clock function section 16, the signal processing section 14 performs arithmetic computation on the measured value and causes the display section 10 to display the value thus obtained (S8: NO, S14: NO, S15: YES, S16, S17). The measured value is displayed in such a manner as indicated by the reference sign d4 in FIG. 3C.

The various data described above is stored in the storage section 15 at substantially the same time as the above-described displaying (S18). In this process, in addition to the data on the measured value and the time of the measurement, reference data corresponding to a flag or an identifier is also stored in the storage section 15. The reference data corresponds to the reference mark indicated by the reference sign d3 and indicates that the measurement of the blood glucose level is performed within a third predetermined period of time from the time of the event. (In this embodiment, the third predetermined period of time is equal to the second predetermined period of time.) Unlike this embodiment, when the device is so designed that the reference data is stored in the storage section 15 by the user's operation on a particular operation switch, the user may forget the operation on the switch and hence the reference data may not be properly stored. According to this embodiment, by contrast, there is no such possibility because the operation to store the reference data in the storage section 15 is performed by the signal processing section 14. The data on the time of the event is also stored in the storage section 15. However, since this data item is already stored in the storage section 15 in step S3, the operation to newly write this data item in the storage section 15 can be omitted.

The data stored in the storage section 15 may be transferred to the personal computer PC to be monitored by a doctor, for example. In addition to the data on the blood glucose level and the time of the measurement, the above-described reference data and the data on the time of the meal may also be transferred to the personal computer PC. This enables the doctor to easily and properly judge the condition of the blood glucose level. Unlike this embodiment, the data on the elapsed time from the time of the meal to the time of the measurement may also be stored in the storage section 15 and transferred to the personal computer PC.

Unlike the above, the measurement of the blood glucose level may be performed after the displaying of the elapsed time and the reference mark is stopped. In this case again, the signal processing section 14 causes the data on the measured value to be displayed and stores the data on the measured value and the data on the time of the measurement in the storage section 15 (S9, S10: YES, S11-S13). In this case, however, unlike the step S18, the reference data and the data on the time of the meal are not stored. Similarly, when the blood glucose level is measured in a state in which the measurement device A is in the event input setting OFF mode (S1: NO) or in a state in which the operation indicating the execution of the event has not been performed, the reference data and the data on the time of the meal are not stored (S2: NO).

Figure 4:
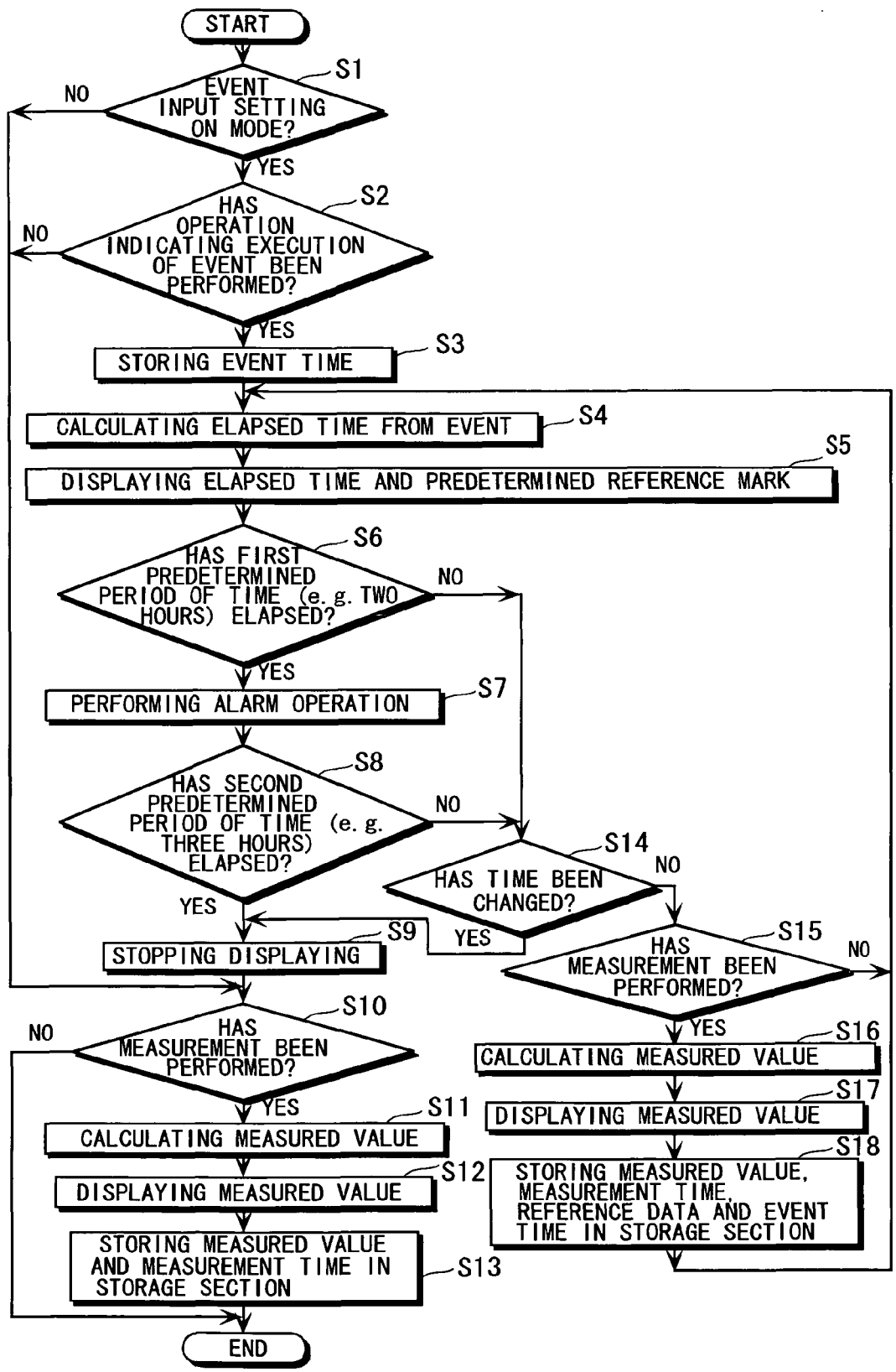
FIG. 4 is a flow chart illustrating an example of process carried out by a signal processing section incorporated in the measurement device shown in FIG. 1.

Though not illustrated in FIG. 4, the measurement device A may be designed as follows. In the case where the operation switch is operated twice with a time interval, the data on the time of the event set by the first operation is invalidated, while the time set by the second operation is determined to be the correct event time. With this arrangement, even when an incorrect time is set by mistake, the correct time can be set later by an easy operation, which is convenient.

The measurement device A may be provided with an edit function which is capable of varying the value of the time of the event or the value of the elapsed time as desired by the user by an operation on a predetermined switch. With this arrangement, even when the user forgets to operate the operation switch 11 and operates the operation switch 11 after elapse of a considerable time from the event, the value of the elapsed time can be varied to a correct value.

The present invention is not limited to the foregoing embodiment. The specific structure of each part of the measurement device according to the present invention can be varied in design in many ways.

The setting of the event time is possible without using the operation switch 11. For instance, the time when the detection switch 19 detects the mounting of the sensor 2 to the sensor mount portion 12 may be determined to be the time of the event. In this case, the measurement device according to the present invention does not need to have the operation switch, similarly to the device disclosed in JP-A-7-128338.

The measurement means according to the present invention needs to be provided with only the function to perform measurement on a particular component contained in a sample, and there is no limitation on the kind of the sample or a specific component to be subjected to measurement. For instance, components in blood other than glucose or a particular component in urine may be subjected to measurement. The display section may be of any design as long as it can display data. Thus, a display other than a liquid crystal display may be employed. The notification means may comprise an alarm lamp or vibrator provided separately from the display section in stead of or in addition to the auditory alarm which sounds an alarm. The "event" used in the present invention is not limited to a meal. For instance, instead of or in addition to a meal, an act such as doing a sport or taking medicine may be set as the event.

The elapsed time from the event time to the current time may be expressed by any other means than numeric characters, and the manner of expression of the elapsed time is not limited. For instance, the elapsed time may be expressed in the form of a bar graph or an image of a clock. In the case where the displaying of the elapsed time is to be stopped upon the elapse of a predetermined period of time from the time of the event, the predetermined period of time may not be fixed to e.g. three hours and may be changed appropriately by the user. The reference mark is not limited to the pattern of a fork, and other patterns, signs or letters may be used.

The invention claimed is:

1. A measurement device comprising:
    a measurement section configured to measure a particular component contained in a sample;
    a clock section configured to clock time;
    a sensor mount section, to which a sensor configured to retain the sample is to be mounted, the sensor mount section including a detection switch configured to detect a mounting of the sensor to the sensor mount section;
    an event time recording section configured to record an event time; and
    a display section configured to display measurement data obtained by a measurement conducted by the measurement device, and the display section also being configured to display an elapsed time, the elapsed time being time between the event time and a current time clocked by the clock
    wherein, when a predetermined operation is performed, the event time recording section regards the time when the predetermined operation is performed as the event time,
    the predetermined operation includes an operation of mounting the sensor to the sensor mount section and causing the detection switch to detect the mounting of the sensor, and
    the event time recording section is configured to be switchable between an event time recording ON mode in which the recording of the event time by detecting the mounting of the sensor is possible and an event time recording OFF mode in which the recording of the event time by detecting the mounting of the sensor is impossible.

2. The measurement device according to claim 1, wherein the elapsed time is displayed on a standby screen of the display section.

3. The measurement device according to claim 1, further comprising
    a notification section configured to perform a notifying operation in a manner that is different from the displaying of the data by the display section,
    wherein the notification section performs the notifying operation when a first predetermined period of time has elapsed from the event time.

4. The measurement device according to claim 1, wherein the displaying of the elapsed time is stopped when a second predetermined period of time has elapsed from the event time.

5. The measurement device according to claim 1, further comprising
    a storage section in which the measurement data obtained by the measurement section is to be stored,
    wherein, when the measurement data is obtained from the measurement performed before elapse of a third predetermined period of time from the event time, reference data indicating to that effect is stored in the storage section as attached to the measurement data.

6. The measurement device according to claim 5, further comprising
    a terminal section configured to read the measurement data obtained by the measurement section and the reference data out of the storage section and outputting the measurement data and the reference data to an external device.

7. The measurement device according to claim 1, further comprising an operation switch, wherein the predetermined operation is an operation to turn on the operation switch.

8. The measurement device according to claim 1, wherein, when the predetermined operation is performed a plurality of times, the time when the operation is performed last is regarded as the event time, and data having been regarded as the event time of an earlier event is invalidated.

9. The measurement device according to claim 1, which is provided with an edit function configured to change at least one of a value representing the event time and a value representing the elapsed time by a predetermined operation.

10. The measurement device according to claim 1, which includes
    a case having a size allowing the case to be held with one hand, the display section being attached to the case so as to be viewable from outside,
    wherein the case accommodates therein devices forming the measurement section, the clock section, the event time recording section and the display section, and entirety of the measurement device is designed as a portable measurement device.

11. The measurement device according to claim 1, wherein the measurement section, the event time recording section and the display section comprise a CPU and a storage section attached to the CPU.

12. The measurement device according to claim 1, wherein the measurement section is configured to measure a blood glucose level.

13. A measurement device comprising:
    measurement means for measuring a particular component contained in a sample;

clock means for clocking time;

sensor mount means for detecting a mounting of a sensor, the sensor mount means being configured to have the sensor mounted thereto, the sensor mount means including a detection means for detecting a mounting of the sensor to the sensor mount means, the sensor being configured to retain the sample;

event time recording means for recording an event time; and a display means for displaying measurement data obtained by a measurement conducted by the measurement means and for displaying an elapsed time, the elapsed time being time between the event time and a current time clocked by the clock means, wherein, when a predetermined operation is performed, the event time recording means regards the time when the predetermined operation is performed as the event time, the predetermined operation includes an operation to mount the sensor to the sensor mount means to cause the sensor mount means to detect the mounting of the sensor, and the event time recording means is configured to be switchable between an event time recording ON mode in which the recording of the event time by detecting the mounting of the sensor is possible and an event time recording OFF mode in which the recording of the event time by detecting the mounting of the sensor is impossible.

14. The measurement device according to claim 1, wherein the event time recording section is configured to record a second event time, the second event time being an operation of an operation switch.

* * * * *